United States Patent [19]

Dunn

[11] 4,027,668
[45] June 7, 1977

[54] MULTI-ANGLE U-SHAPED HUB FOR INFUSION MEMBER

[76] Inventor: Allan R. Dunn, 1160 Kane Concourse, Miami Beach, Fla. 33154

[22] Filed: Dec. 10, 1975

[21] Appl. No.: 639,411

[52] U.S. Cl. .................... 128/214 R; 128/214.4; 128/349 R
[51] Int. Cl.² .................. A61M 5/00; A61M 25/02
[58] Field of Search ........ 128/214 R, 214.2, 214.4, 128/221, 347, 348, 349 R, DIG. 16, DIG. 26

[56] References Cited

UNITED STATES PATENTS

| | | | |
|---|---|---|---|
| 2,268,321 | 12/1941 | Flynn | 128/349 R X |
| 2,727,513 | 12/1955 | Muller | 128/DIG. 26 |
| 3,090,384 | 5/1963 | Baldwin et al. | 128/221 |
| 3,138,158 | 6/1964 | Gordon et al. | 128/DIG. 26 |
| 3,194,235 | 7/1965 | Cooke | 128/214 R X |
| 3,297,030 | 1/1967 | Czorny et al. | 128/214.4 |
| 3,585,986 | 6/1971 | Krug | 128/221 |
| 3,628,813 | 12/1971 | Lee et al. | 128/214 R X |
| 3,630,195 | 12/1971 | Santomieri | 128/214 R X |
| 3,683,911 | 8/1972 | McCormick | 128/214 R |
| 3,722,508 | 3/1973 | Roberts | 128/214 R X |
| 3,812,851 | 5/1974 | Rodriguez | 128/214 R X |
| 3,853,126 | 12/1974 | Schulte | 128/214 R |
| 3,870,043 | 3/1975 | Dunn | 128/214 R |
| 3,942,528 | 3/1976 | Loeser | 128/214 R |

FOREIGN PATENTS OR APPLICATIONS

| | | | |
|---|---|---|---|
| 1,278,429 | 10/1961 | France | 128/221 |
| 1,285,953 | 1/1962 | France | 128/348 |
| 1,490,616 | 6/1967 | France | 128/214 R |
| 818,246 | 10/1951 | Germany | 128/221 |
| 1,273,547 | 5/1972 | United Kingdom | 128/214.4 |
| 809,146 | 2/1959 | United Kingdom | 128/221 |
| 1,024,410 | 3/1966 | United Kingdom | 128/214.4 |

*Primary Examiner*—Edgar S. Burr
*Assistant Examiner*—Paul T. Sewell
*Attorney, Agent, or Firm*—Ostrolenk, Faber, Gerb & Soffen

[57] ABSTRACT

A U-shaped hub has a plurality of clips formed along its exterior periphery to selectively receive an infusion tube at one of a like plurality of fixed angles relative to a protrusion extending from the periphery of the hub. The junction of the infusion tube and a hollow infusion member, such as an intravenous needle, a sheathed needle, a catheter, a cannula, a styletto-catheter or the like, is embedded within the hub projection. The channel diameter of each hub clip is substantially equal to the outer diameter of the flexible infusion tube to prevent collapse of the tube wall while enabling the initially straight tube to be bent and retained at one of a plurality of angles with respect to the center line of the infusion member to permit the use of a direct tubing connection between an intravenous source and the infusion member and for reducing the danger of lateral movement of the infusion member relative to the body. A novel styletto-catheter having a slidably retractable but non-removable stylette positioned in a separate channel within the wall of the catheter lumen is disclosed for use either with or without the U-shaped hub. The non-removable stylette prevents kinking, twisting and shape-distortion of the infusion member after the insertion thereof.

16 Claims, 17 Drawing Figures

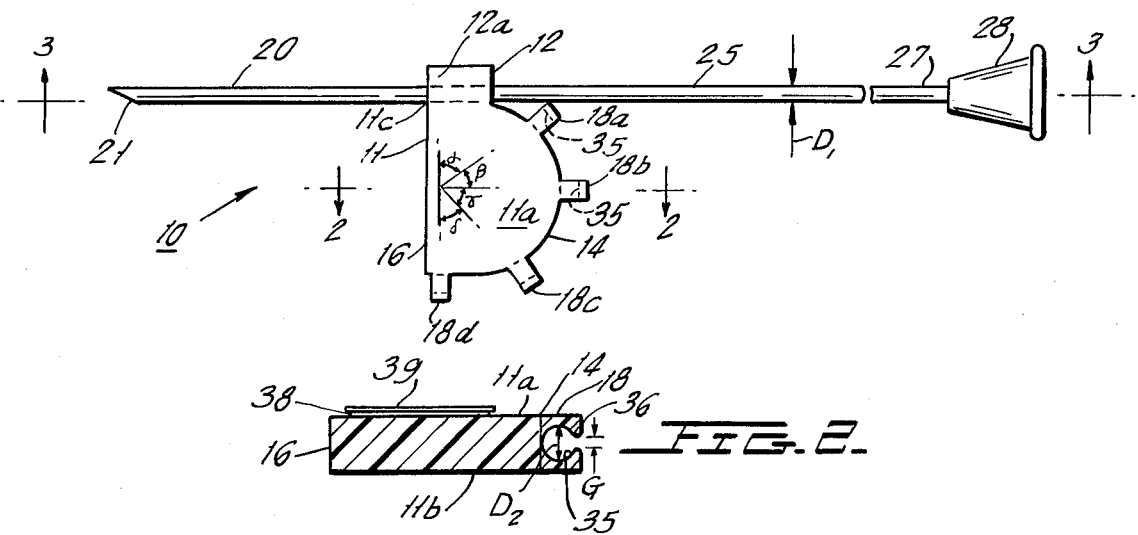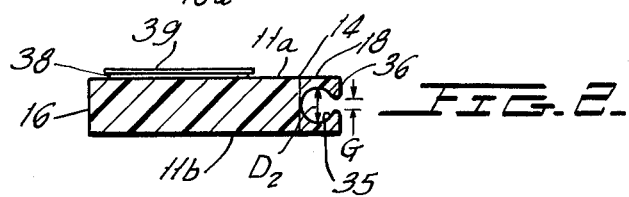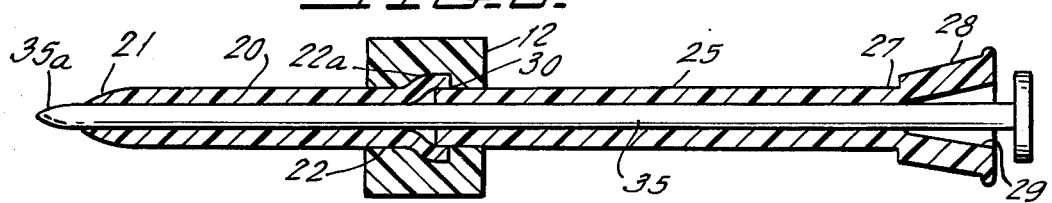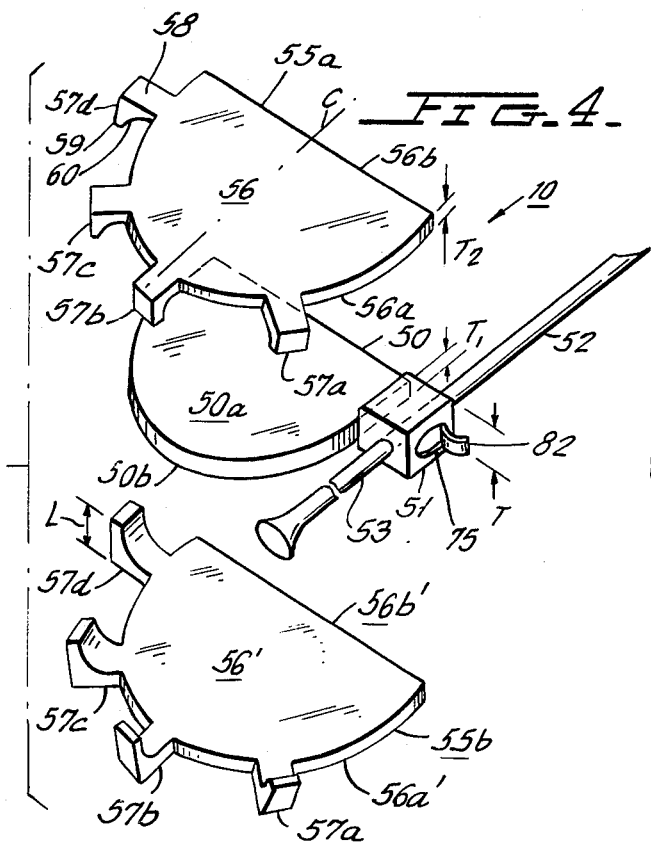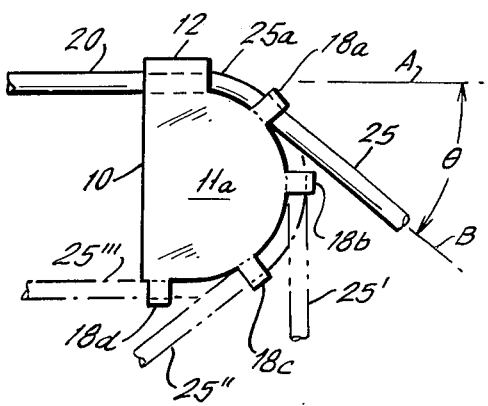

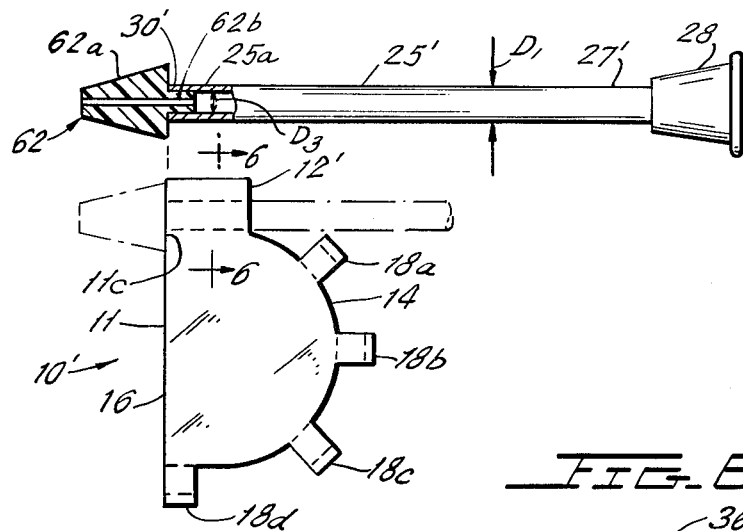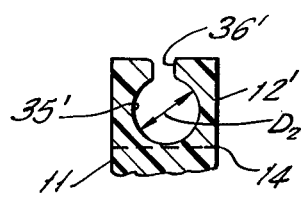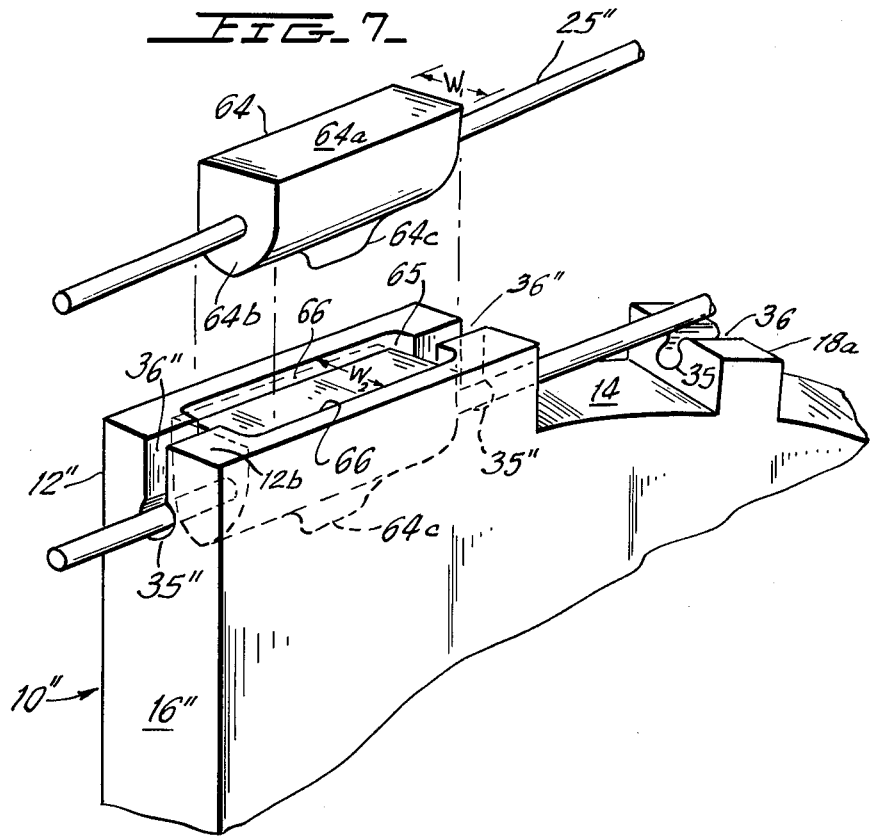

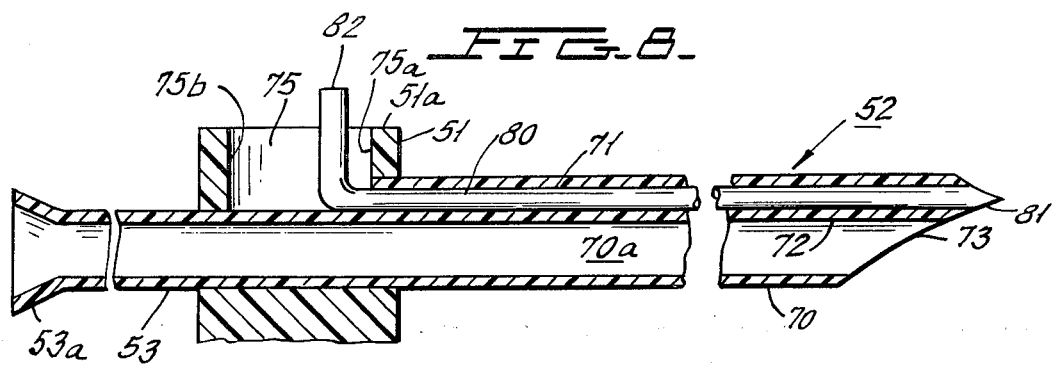
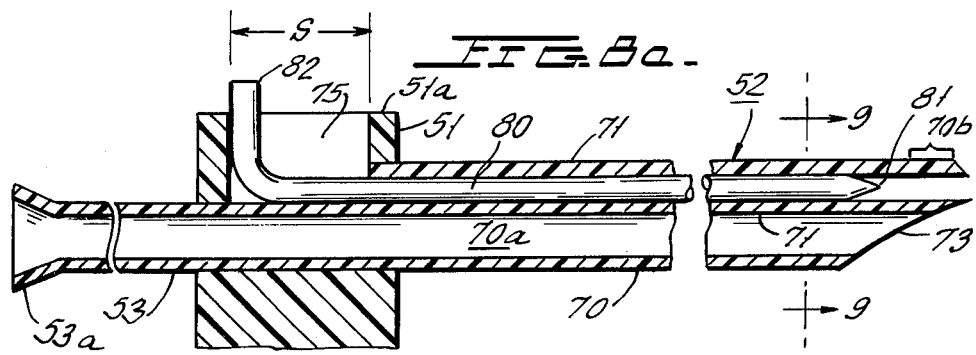
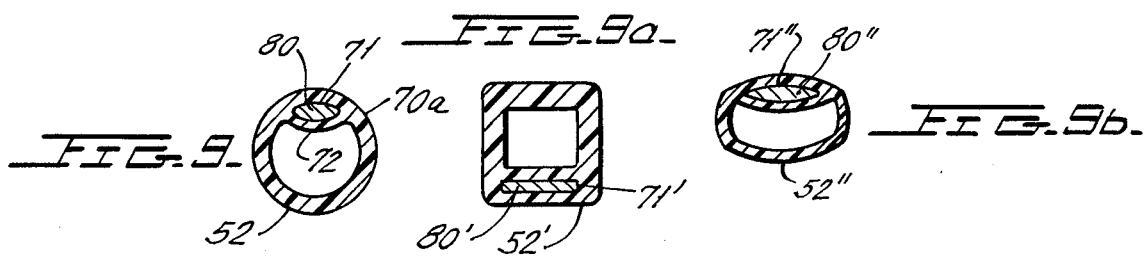
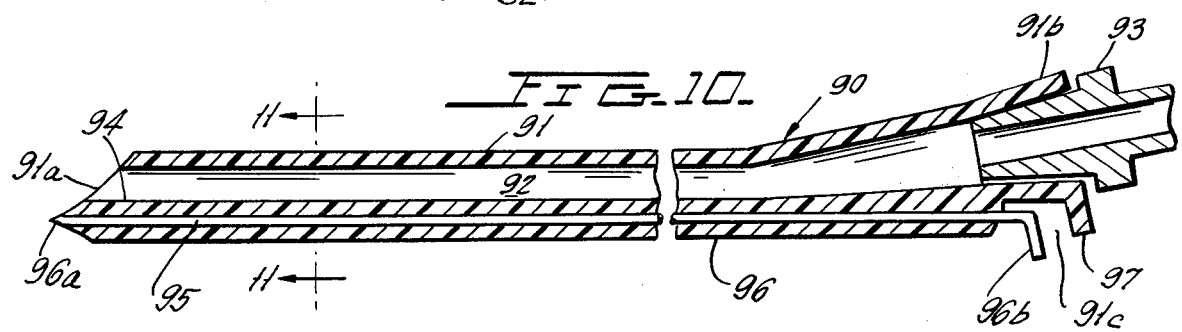
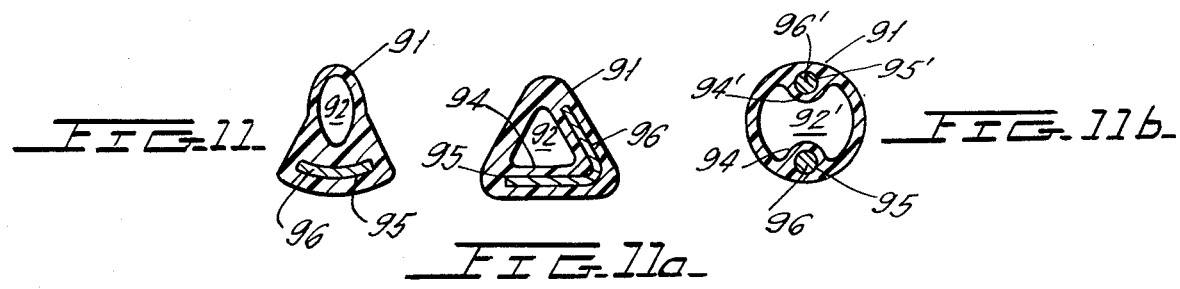

MULTI-ANGLE U-SHAPED HUB FOR INFUSION MEMBER

BACKGROUND OF THE INVENTION

The present invention relates to infusion members and more particularly to a novel multi-angle U-shaped hub for an infusion member.

Conventional medical practice often requires an intravenous infusion to be performed to allow blood, nutriments or other desirable fluids to be fed directly into the vascular system of a patient being treated. A venipuncture is performed at a site on the patient's body and a hollow infusion member is inserted therethrough. Typically, a length of tubing is attached between the infusion member and a supply bottle located in the vicinity of the patient. It is extremely important to prevent lateral movement of the infusion member relative to the venipuncture site, to reduce abrasion and laceration of the flesh around the venipuncture site and so minimize its irritation and susceptibility to phlebitis, and to prevent inadvertent withdrawal of the infusion member, to minimize hematoma or blood loss.

It is known to provide a structure, adjacent to the junction of the infusion member and tube, to be grasped during the venipuncture operation. It is also known to utilize the structure to provide a surface for taping the junction region to the patient's body, after the infusion member had been inserted, to reduce the undesirable lateral movements thereof.

Desirable infusion apparatus should also utilize a structure allowing the infusion member and tube to be manufactured in an axially aligned condition, and still provide a doctor or technician complete choice of the final angular orientation of the infusion tube with respect to the infusion member. A medical practitioner, especially when preparing a patient for surgery, requires a choice of angles of the infusion tube relative to the infusion member. Various surgical procedures require that the infusion tube: remain axially aligned with the infusion member, as when the intravenous supply is positioned toward the lower extremity of the patient; have a 90° bend with respect to the axis of the infusion member, as when filters are attached thereto; have a 135° bend with respect to the infusion member axis, to allow the flexible tube to point towards the head of the operating table when the venipuncture site is situated in the outstretched arm of the patient; or have a 180° bend if the arm is at and parallel to the patient's side and the intravenous source is near the head of the patient. Thus, an infusion member hub capable of maintaining the flexible infusion tube at one of a plurality of angles relative to the axis of the infusion member, yet minimizing the radial pressure on the tube to prevent a pinch effect and subsequent decrease of both internal cross-section of and flow through the tube, is desirable.

BRIEF SUMMARY OF THE INVENTION

In accordance with the invention, a multi-angle U-shaped hub for an infusion member includes a plurality of clips generally equally spaced about the periphery of the hub and a projection extending from one corner of the hub to receive the junction of the infusion member, such as an intravenous needle, a sheathed needle, a cannula, a catheter, a styletto-catheter or the like, with a flexible length of infusion tube. The infusion tube and infusion member are initially in axial alignment. Each of the hub clips has a radially disposed slot, of a width less than the outer diameter of the tube, which slot communicates with a generally circular aperture having a diameter at least equal to the outer diameter of the flexible tube and formed in each hub clip parallel to the hub periphery. The infusion tube is inserted through the slot into the aperture of a successively larger total of the hub clips to enable the tube to be bent through and maintained at successively greater angles relative to the axis of the infusion member. The diameter of the aperture is selected to prevent pinching of the wall of the infusion tube.

In a preferred embodiment, a semi-circular hub is provided with four hub clips. Each clip is positioned to have a 45° angular rotation along the curved hub periphery relative to the adjacent hub clips or to the hub protrusion.

In another preferred embodiment, the hub protrusion encloses the junction between the flexible infusion tube and a male standard cannula connector to provide the advantages of the multi-angle hub while enabling the practitioner to select one of a variety of standard rigid or flexible cannulae for attachment to the standard connector.

In still another preferred embodiment, a shaped collar is formed about the junction of the infusion member and infusion tube, or an intermediate portion of an infusion combination. The hub protrusion includes a flanged recess adapted to forcefittedly receive and lock the shaped collar to the multi-angle hub, thereby enabling insertion and removal of one of a plurality of infusion combinations, and reuse of the hub and/or infusion member.

In yet another preferred embodiment, the infusion member is a single lumen catheter having a slidably retractable but non-removable stylette contained in a secondary channel formed completely within the catheter wall; the hub protrusion includes a cooperatively formed recess in communication with the stylette channel for enabling the passage of the proximal end of the stylette through the protrusion whereby the sharp stylette tip may be withdrawn a short distance into its secondary channel after the venipuncture has been performed. This novel stylett-catheter may be utilized separate from the novel hub.

Accordingly, it is an object of the present invention to provide a novel hub for an infusion member and infusion tube.

It is another object of the present invention to provide a novel infusion hub allowing an infusion tube to be maintained at one of a plurality of angular orientations with respect to the axis of an infusion member.

It is yet another object of the present invention to provide a hub having means for detachably receiving one of a variety of infusion tube-infusion member combinations to provide for reuse of the hub.

It is a further object of the present invention to provide a novel styletto-catheter having its stylette slidably received within a secondary channel formed within the wall of a single lumen catheter.

It is a still further object of the present invention to provide a styletto-catheter in apparatus allowing a flexible infusion tube to be maintained at one of a plurality of angular orientations with respect to the axis of the catheter lumen.

These and other objects of the present invention will become apparent in reading the accompanying detailed description and the drawings.

BRIEF DESCRIPTION OF THE DRAWINGS

FIG. 1 is a plan view of a multi-angle U-shaped hub for an infusion member and infusion tube in accordance with the principles of the present invention.

FIG. 1a is a plan view of the hub of FIG. 1 and illustrating the manner in which the infusion tube is retained at a plurality of angular orientations with respect to the axis of the infusion member;

FIG. 2 is an enlarged cross-sectional view of the hub taken along line 2—2 of FIG. 1;

FIG. 3 is an enlarged cross-sectional view of the hub, infusion member and infusion tube taken along line 3—3 of FIG. 1;

FIG. 4 is an exploded perspective view of the hub utilizing a novel styletto-catheter and illustrating a method for the manufacture thereof;

FIG. 5 is a plan view of another embodiment of hub having means for detachable mounting an infusion combination to the hub protrusion, and a partially-sectionalized view of one such infusion combination;

FIG. 6 is an enlarged cross-sectional view of the hub taken along line 6—6 of FIG. 5;

FIG. 7 is an exploded perspective view of another means for detachably mounting an infusion combination to a protrusion on the periphery of the multi-angle hub of the present invention;

FIGS. 8 and 8a are cross-sectional views of the hub and novel styletto-catheter in the extended and retracted conditions, respectively;

FIG. 9 is a cross-sectional view of the styletto-catheter taken along line 9—9 of FIG. 8a;

FIGS. 9a and 9b are cross-sectional views of alternative embodiments of the styletto-catheter;

FIG. 10 is a cross-sectional view of another embodiment of a styletto-catheter in accordance with the principles of the invention and for use separate from the U-shaped hub;

FIG. 11 is a cross-sectional view of the styletto-catheter taken along line 11—11 of FIG. 7; and FIGS. 11a and 11b are cross-sectional views of alternative embodiments of the styletto-catheter utilizing the principles of the present invention.

DETAILED DESCRIPTION OF THE INVENTION

Referring now to FIGS. 1—3, a preferred embodiment of multi-angle U-shaped hub 10 comprises a generally semicircular portion 11 formed of a relatively inflexible and lightweight material, such as plastic or the like, and having generally parallel upper and lower smooth surfaces 11a and 11b, respectively. A projection 12 integrally extends from a portion of hub periphery 14 adjacent to a first corner 11c formed between the periphery and the diametric edge 16. A plurality of clips 18a–18d respectively extend radially outward from hub periphery 14.

A hollow infusion member 20, such as a needle; a cannula; a catheter with or without centrally placed removable trochar, stylette or needle; a sheathed needle; a styletto-catheter or the like, has a bevelled or flat distal end 21 and a proximal end 22 having attachment means 22a such as a flared skirt, hub or the like. A length of flexible infusion tubing 25 has an outer diameter $D_1$. One end 27 of the tube includes hub means 28, such as a standard universal female intravenous tube coupling having a converging interior passage 29 for force-fittingly receiving the nipple, such as a Luer fitting or the like, of a tube running from an intravenous supply bottle or the like (not shown for reasons of simplicity). The proximal end 22 of infusion member 20 is adapted to closely receive and form a substantially liquid-tight seal to a forward end 30 of tube 25. It should be understood that a separate infusion member 20 and infusion tube 25 are shown for the purposes of illustration only; the wall and channel of tube 25 may extend in uninterrupted fashion completely through hub protrusion 12 to form a flexible cannula, as the hollow infusion member 20. In general, hub protrusion 12 receives an infusion combination, which combination is defined herein as any infusion tube in fluid-flow connection with either an infusion member or means for coupling an infusion member to the tube. Usually a more rigid stylette or hollow needle is kept within the infusion member during insertion and removed after insertion in the vein.

Hub protrusion 12 surrounds and encases the junction between infusion member proximal end 22 and infusion tubing forward end 30. The protrusion is preferably molded around the previously joined infusion member and tube to provide a high quality liquid-tight seal.

Each hub clip 18 has a selected value of angular rotation along curved periphery 14 with respect to both the adjacent hub clips and to a reference line 12a at protrusion 12. Thus, a first clip 18a is situated at an angle α with respect to reference line 12a; a second clip 18b is situated with an angle β with respect to first clip 18a; a third clip 18c is situated with an angle γ with respect to second clip 18b; and a fourth clip 18d is situated with an angle δ with respect to third clip 18c, for hub having four hub clips 18. It should be understood that this novel hub for infusion member may be provided with one clip, or plurality of clips 18 and that the angles formed between adjacent clips and between a clip and the hub protrusion may be selected as required for a range of end uses. In a preferred embodiment, the hub includes four clips having equal angles with each other and with reference line 12a, i.e., α=β=γ=δ, and each angle is approximately 45°.

Each hub clip 18 has an aperture 35, of diameter $D_2$, formed therethrough parallel to hub periphery 14. Aperture diameter $D_2$ is selected to be substantially equal to, but never less than, the outer diameter of $D_1$ of infusion tube 25, whereby pressure tending to pinch infusion tube 25 partially or completely closed is avoided when the infusion tube is positioned within aperture 35. A slot 36 is formed through the radially outermost remaining portion of clip 18 to allow tube 25 to be pressed into aperture 35. Slot 36 has a gap distance G selected to allow tube 25 to pass therethrough only when tube 25 is forcibly compressed, whereby the tube is maintained within the aperture if external compression force is not applied. Preferably, the material utilized for the formation of the hub, and particularly for clips 18, is highly resilient to absorb shock forces tending to tear tube 25 from each clip 18 through which the tube has een positioned.

In use, opposite surfaces 11a and 11b of the hub are grasped to allow insertion of infusion member 20. A solid or hollow trocar member 35 may be required to perform the puncture, particularly if the infusion member 20 is a flexible catheter or the like. The bevelled cutting edge 35a of the trocar is inserted through the axially aligned lumens of tube 25 and infusion member 20 to extend forward of infusion member forward end 21. After the puncture has been performed, and the trocar removed, infusion tube coupling 28 is attached to a supply bottle or the like (not shown). It should be understood that known means may be employed with tube 25 and its coupling 28 to temporarily seal the lumen and prevent liquid outflow after the puncture has been completed but before connection has been made to the coupling. One of smooth hub surfaces 11a or 11b is then placed against the patient's skin and the hub is secured in place by means external to the hub (not shown). Alternatively, surfaces 11a and/or 11b may be slightly concave to make pinching more comfortable. And in another alternative, one or both of hub surfaces 11a, 11b are coated with a layer of adhesive material 38 and covered with a protective layer 39; protective layer 39 is removed and hub 10 is pressed against the patient's skin to allow adhesive layer 38 to adhere thereto and hole the hub in place to absorb the forces of lateral movement.

Having inserted infusion member 20 and secured hub 10 to the patient's body, the physician or medical technician now bends tube 25 into position against the slot 36 formed in the first clip 18a and presses the tubing therethrough to be retained within aperture 35 (FIG. 1a); the axis B of infusion tube 25 is now held at a bend angle $\theta$ with respect to the axis A of infusion member 20, having been gently bent at region 25a to prevent buckling of the tube wall and ensuing diminution of infusion flow. A larger bend angle $\theta$ is achieved as tube 25 is engaged within the apertures of clips 18 having greater angles of rotation from protrusion 12. Thus, in the illustrative examples, $\theta$ is 45° when tube 25 is held only by clip 18a. Tube 25' forms an angle $\theta$ equal to 90° when positioned in the apertures of both clips 18a and 18b; $\theta = 135°$ when tube 25'' is positioned in the apertures of clips 18a, 18b and 18c; and $\theta = 180°$ when tube 25''' is positioned through the apertures of all four clips 18a–18d.

In one preferred embodiment (FIG. 4), multi-angle hub 10 is formed of a semi-circular blank 50 having a thickness $T_1$. Protrusion 51, having a greater thickness T, is formed along the curved periphery of member 50 and encloses the junction between an infusion member 52, such as a styletto-catheter, and an infusion tube 53. Each or a pair of matched clip members 55a and 55b has a central semi-circular portion 56 and 56', respectively, of thickness $T_2$ and have a like plurality of fingers 57 extending from their respective curved peripheries 56a and 56'a of portions 56 and 56' – the position of clip fingers 57a–57d on each of periphery 56a, 56'a being complementary about an axis C passing through the midpoint of each diametric side 56b'; 56b' and perpendicular thereto. Each clip finger 57 includes a radially extended portion 58 integrally joined to a semi-circular portion 56 or 56' and a second portion 59 extended perpendicular to the plane of the portion at the radially outermost end of first portion 58. A curved portion 60 fills the inside corner formed by portions 58 and 59 and has a radius of curvature essentially equal to one-half the outer diameter $D_1$ of tube 25.

A matched pair of clip members 55a and 55b are arranged with their respective clip finger second portions 59 facing each other, and are fastened by means of a suitable cement, solvent, thermal weld or the like to opposite ffaces 50a, 50b of hub member 50. It should be evident that a large selection of final hub assemblies 10 can be formed by manufacturing a plurality of different hub members 50 and another plurality of different matched pairs of clip members 55. Each hub member 50 has a particular combination of infusion member 52 and length and type of infusion tube 53 and may be utilized with a pair of matched clip members 55 selected from the plurality of such clip member pins having the same radius but utilizing different numbers and positions of clip portions 57. The clip member thickness $T_2$ and hub member thickness $T_1$ are selected such that $T_1 = T_2 = T$, the protrusion thickness, to yield a hub having smooth upper and lower surfaces 11a, 11b (FIG. 2). The length L of each clip second portion 59 is selected according to the formula $L = \frac{1}{2}(T-G)$ to provide for a suitable slot 36 through which tube 25 may enter the clip.

Referring now to FIGS. 5 and 6, wherein like reference numerals are utilized for like elements, another embodiment of multi-angle infusion hub 10' includes a hub protrusion 12' integrally extended from a portion of hub periphery 14 adjacent to the first corner 11c formed between the periphery and diametric edge 16. Hub protrusion 12' has a cross-section similar to each hub clip 18 and includes an aperture 35 of diameter $D_2$ formed therethrough parallel to hub periphery 14 and a slot 36' formed through the radially outermost remaining portion of hub protrusion 12'. An intermediate portion 25a of tube 25', between distal end 30' and proximal end 27', is forcibly compressed and inserted within protrusion aperture 35' and maintained therein by the resiliency of the material forming protrusion 12', in the absence of external compression force.

A male standard cannula connector 62 has a converging forward portion 62a and a tube coupling portion 62b of reduced diameter force-fittedly received within the lumen of distal end 30 of infusion tube 25'. Portion 62 may also be cemented, bonded by solvent or thermally welded to distal end 30. The outer diameter $D_3$ of coupling portion 62b is at least equal to the bore diameter of flexible tubing 25', to insure a liquid-tight connection therebetween. The standard connector 62 is adapted to accept a wide variety of rigid or flexible standard cannulae (not shown). If force-fittedly secured, the selected cannula may be removed from standard connector 62 to allow the hub, tube and connector combination to be reused, or the tube-connector combination may be pressed outwardly from channel 35' and be disposed of, allowing reuse of hub 10'.

Referring now to FIG. 7, a collar 64 has a flat upper surface 64a of width $W_1$ and a tapering lower portion 64b having a keel-like projection 64c to control rolling or turning. The collar may be molded around the junction between an infusion member and infusion tube to provide the required liquid-tight connection, or, as illustrated, may be molded about an intermediate portion of a continuous length of flexible infusion tube 25'' to form part of an infusion combination. Hub member 10'' has a flat surfaced diametric edge 16'' and includes a hub protrusion 12'' having a recess 65 of similar cross-section to collar 64 including keel 64c. Recess 65 is formed into protrusion 12'' perpendicular to flat surface 16''. A circular channel 35'' axially extends in either direction from recess 65 and a slot 36'' is formed through the radially outermost remaining portion of hub protrusion 12'' to allow tube 25'' to enter channel 35''. A flanged edge 66 is formed along the length of the rectangular opening of recess 65 in the radially outermost surface 12b of hub protrusion 12'. The flanged edges reduce the width of recess 65 to a width $W_2$ less than the width $W_1$ of the remaining portion of the recess and of collar 64.

In use, collar 64 is pressed into recess 65 with its keel 64c and then its converging portion 64b initially entering the recess. The insertion is aided by the resiliency of the material utilized for the hub member. Upon further application of force, collar 64 fully enters recess 65 and flange portion 66 resiliently snap-locks over peripheral edge portions of the top surface 64a of molded collar 64, to prevent radial movement of collar 64 within recess 65, while the remaining portions of hub protrusion 12" prevent axial and rotational movement of the collar and the encased tube 25". The resilient material of hub protrusion 12" is forced apart adjacent top surface 12 to allow collar 64 and the attached tube 25" to be removed from recess 65 and discarded whereby multi-angle hub 10" may be reused.

I have found that a particularly advantageous infusion member for use with my novel, multi-angle U-shaped hub 10 is a styletto-catheter 52 (FIG. 8) having a generally flexible infusion portion 70 integrally joined with infusion tube 53 which is of variable length and has a female I.V. connection at proximal end 53a. Infusion portion 70 has a smooth exterior surface 70a and may be of any geometric cross-section, including circular (FIG. 9), square (FIG. 9a), oval (FIG. 9b) or triangular (FIG. 11a) cross-section. A secondary channel 71 is formed within a thickened portion 72 of the tube wall and extends parallel to the lumen of infusion member 52 from distal end 73 into a communicating recess 75 formed in hub member protrusion 51. The cross-sectional area of secondary channel 71 is usually, but not always, less than the cross-sectional area of catheter lumen 70a whereby the magnitude of lumenal flow is at most slightly reduced.

A semi-rigid metallic stylette 80 has a cross-sectional shape selected to be closely received within the bore of secondary channel 71. Thus, a first stylette 80 has an oval cross-section for use in oval cross-section secondary channel 71 formed in a portion of the wall 72 of a circular cross-section catheter 52 (FIG. 9); another catheter 52' of square cross-section (FIG. 9a) has a secondary channel 71' formed with a rectangular cross-section to closely receive a stylette 80' having a cooperative rectangular cross-section; and a third catheter 52" (FIG. 9b) has a secondary channel 71" of highly eccentric oval cross-section to closely receive a stylette 80" having a cooperative oval cross-section.

The distal end 81 of stylette 80 is bevelled and sharpened to enable a venipuncture to be performed even when infusion portion 70 is formed of a flexible material. Stylette 80 is bent to allow its proximal end 82 to extend through recess 75 in a direction substantially perpendicular to the axial direction of infusion member 52 and away from the top surface 51a of protrusion 51.

The length of stylette 80 is selected to allow distal end 81 to extend forward of catheter end 73 when stylette extension 82 is urged against the forward wall 75a of recess 75. The length S of recess 75 is selected to allow complete withdrawal of distal end 81 within secondary channel 71 when extension 82 is urged against the rear walls 75b of recess 75. Stylette 80 cannot be removed in normal use and remains rigidly positioned within secondary channel 71 to resist and prevent kinking and twisting movement of infusion portion 70, while distal end 81 is enclosed and protected by the forward portion 70b of the catheter whereby danger of laceration to the surrounding tissue is reduced. The width of a styletto 80 may be maximized for formation of a puncture having a size approaching the cross-sectional area of the catheter, for ease of insertion thereof.

In another preferred embodiment, a styletto-catheter 90 (FIG. 10) is utilized independent of hub 10. Stylet-to-catheter 90 comprises a flexible tube 91 having a catheter lumen 92 generally axially formed therethrough. Tube 91 has a bevelled distal end 91a and a flared proximal end 91b adapted to force-fittingly receive a standard male intravenous coupling 93 in axial connection. A portion 94 os the catheter wall is gradually thickened to extend into lumen 92. At least one secondary channel 95 is axially formed within thickened wall portion 94. A flexible stylette member 96 is positioned within each secondary channel 95. The distal end 96a of stylette 96 is sharpened to enable formation of a venipuncture or the like, and the proximal end 96b of stylette 96 is bent to extend radially away from the axis of lumen 92. A recess 91c is formed in the wall of catheter 91 adjacent to stylette extension 96b to enable the stylette to be urged toward catheter tip 91a until stylette tip 96a protrudes therefrom for the cutting operation. The stylette is withdrawn along secondary channel 95 only until stylette extension 96b abuts a protrusion 97, to prevent complete removal of the stylette. It should be understood that the resiliency of the material utilized in the formation of catheter 91 is sufficiently high to cooperate with the exterior surface of stylette 96 to form a liquid-tight seal to prevent fluid passage along the second channel.

Styletto-catheter 90 may utilize a single stylette 96 emplaced within a single secondary channel 95 (FIGS. 11 and 11a), or may advantageously utilize a pair of independently movable stylettes 96, 96' (FIG. 11b), each independently slidably enclosed within its own secondary channel 95, 95' formed within a like number of thickened portions 94, 94' in the wall of the catheter.

The shape, number and position of the stylettes are chosen for the required end use. The cross-sectional area of the thickened wall portion 94 (of 71 of FIG. 8 and 8a), and hence of stylette 80 or 96, may be selected to decrease the cross-sectional area of the lumen 92 of the catheter by an insignificant amount, or may be selected to allow use of a stylette 96 having a greater width than the width of the lumen 92, to form a large area puncture for ease of catheter insertion. Each stylette may advantageously be V-shaped (FIG. 11a) to cut a flat of skin, to even further enlarge the puncture area for ease of catheter insertion.

There has just been described a novel, multi-angle U-shaped hub for an infusion member and tube, allowing the infusion tube to be maintained at one of a plurality of angular orientations with respect to the axis of the infusion member. A novel styletto-catheter having its stylette slidably received within a secondary channel formed within a wall of a single-lumen catheter is described, which styletto-catheter may be used either with the U-shaped hub or independently.

The present invention has been described in connection with several preferred embodiments thereof; many variations and modifications will now become apparent to those skilled in the art. It is preferred, therefore, the present invention be limited not by the specific disclosure herein, but only by the appended claims.

What is claimed is:

1. A hub for use with an infusion combination including a flexible infusion tube having a first end in fluid-flow connection with hollow infusion means and having a second end including means for forming another fluid-flow connection to an infusion supply, said hub comprising:
- a hub member having a generally semicircular shape and having a protrusion radially extended away from its curved periphery;
- a first portion of said flexible tube being secured through said hub protrusion;
- clip means integrally jointed to said hub member and positioned along its curved periphery at a location spaced from said hub protrusion for selectively receiving a second portion of said flexible tube intermediate said first portion and said second end to selectively maintain the axis of said flexible tube at a selected angular orientation relative to the axis of said hollow infusion means.

2. Apparatus as set forth in claim 1, wherein said clip means comprises a clip member having an aperture formed therethrough generally parallel to the curved periphery of the hub member and having a slot communicating between said aperture and an exterior surface of the clip member, the gap distance of the slot being less than the diameter of the associated aperture.

3. Apparatus as set forth in claim 2, wherein said infusion tube has a selected outer diameter and the diameter of said aperture in said clip member is substantially equal to the outer diameter of said tube.

4. Apparatus as set forth in claim 1, wherein said hub includes a plurality of clip means, each said clip means being integrally joined to said hub member and being positioned along its curved periphery at a location spaced from said hub protrusion and the remaining said clip means for selectively receiving a different portion of said flexible tube, each said different portion being intermediate said first portion and said second end, to selectively maintain the axis of said flexible tube at a selected angular orientation relative to the axis of said infusion means.

5. Apparatus as set forth in claim 4 wherein each said clip means comprises a clip member disposed along the curved periphery of said hub member, said clip members being disposed along the curved periphery of said hub member with progressively greater angular orientations relative to a reference line between a point on said hub member protrusion and the center of the first periphery of said hub member.

6. Apparatus as set forth in claim 5, wherein the angular orientations are substantially equal between adjacent clip members and between the clip member nearest to said protrusion and the reference line on said protrusion.

7. Apparatus as set forth in claim 6, wherein four clip members are disposed about the periphery of said hub member and said angular orientation is approximately equal to 45°.

8. Apparatus as set forth in claim 4, wherein said clip means comprises a pair of first and second clip members each having a generally semicircular central portion; a plurality of clip fingers extending from the curved perihery of each said central portion, each clip finger including a radially extended portion integrally joined to the semicircular portion and a second portion extending perpendicular to the plane of the radially extended portion at the radially outermost end thereof; the clip fingers of said first and second clip members being positioned along the respective curved peripheries in complementary fashion; said first and second clip members being secured to opposite faces of said hub members with said clip finger second portions extending toward but not meeting each other to form a plurality of tube-retaining clips.

9. Apparatus as set forth in claim 1, wherein said hollow infusion means is an infusion member having distal and proximal ends, said distal end of said infusion member being adapted for performing a venipuncture in a patient's extremity; said proximal end of said infusion member closely receiving said first end of said flexible infusion tube to form at least a partially liquid-tight seal therebetween; said hub protrusion enclosing the junction between said infusion member and said tube in a liquid-tight manner.

10. Apparatus as set forth in claim 1, wherein said flexible infusion tube has a selected outer diameter; said hub protrusion has an aperture of substantially equal diameter to the outer diameter of said flexible tube, said aperture being formed therethrough generally parallel to the curved periphery of said hub member; said protrusion having a slot in communication between said aperture and an exterior surface of said hub protrusion, the gap distance of the slot being less than the outer diameter of said flexible tube; said first portion of said flexible tube being compressively insertable into and removable from said aperture through said slot.

11. Apparatus as set forth in claim 10, wherein said infusion means is a cannula coupling member having a tubular portion inserted into the bore of said flexible tube to form a coaxial liquid-tight seal therebetween, the region of said flexible tube bounding said seal being said first portion of said tube inserted into said aperture in said protrusion.

12. Apparatus as set forth in claim 1, wherein said infusion combination further comprises a shaped collar molded about said first portion of said flexible tube; said hub protrusion further including a recess formed into a first surface thereof and having substantially the same shape as said collar; a pair of opposed resilient flanges extending partly across said recess adjacent to said first surface; said flanges being adapted to be compressed to allow said collar to enter said recess and to resiliently snap over said collar when said collar has completely entered said recess, thereby preventing removal of said collar from said recess.

13. Apparatus as set forth in claim 1, wherein said infusion means is a styletto-catheter comprising a single lumen flexible catheter having a first and enclosed by said hub protrusion and a second end; said catheter having a secondary channel formed in a thickened axial portion of its wall; a substantially rigid stylette closely received within said secondary channel; said stylette having a sharpened distal end and a proximal end, said proximal end extending at an angle to the axis of said stylette; said hub protrusion including a recess in communication with said secondary channel to enable said proximal end of said stylette to move between first and second positions, respectively, to position the distal end of said stylette respectively extended beyond said second end of said catheter and retracted into the bore of said secondary channel adjacent said second end.

14. Apparatus as set forth in claim 1, wherein said hub member has a flat surface substantially parallel to a plane passing through said hub protrusion and said clip means; and adhesive means on said flat surface for fastening said hub to the patient's extremity adjacent to the venipuncture site.

15. A styletto-catheter for use with medical infusion apparatus, comprising: a single lumen flexible catheter having a distal end and a proximal end, said proximal end including means for forming a fluid-flow connection with said medical infusion apparatus; said catheter having a first secondary channel formed in a first thickened wall portion of said catheter; a first substantially rigid stylette having a sharpened distal end and a proximal end, said proximal end of said first stylette extending at an angle with respect to the axis of said first stylette; said first stylette being closely received for axial movement within said first secondary channel; said catheter having a recess adjacent to said proximal end of said first stylette and in communication with said first secondary channel to enable said proximal end of said stylette to move between first and second positions to enable said distal end of said first stylette to be respectively extended beyond and retracted into the bore of the first and secondary channel and means for preventing said stylette from being removed from said first secondary channel.

16. A styletto-catheter as set forth in claim 15, further comprising a second secondary channel formed in another thickened axial portion of the wall of said catheter, said secondary channel being spaced from said first secondary channel; a second stylette substantially similar to said first stylette; said second stylette being closely received within said second secondary channel for axial movement independent of the movement of said first stylette.

* * * * *